United States Patent [19]
Logothetis et al.

[11] Patent Number: 4,840,913
[45] Date of Patent: Jun. 20, 1989

[54] OXIDES OF NITROGEN DETECTOR

[75] Inventors: Eleftherios M. Logothetis, Birmingham; Richard E. Soltis, Redford, both of Mich.

[73] Assignee: Ford Motor Company, Dearborn, Mich.

[21] Appl. No.: 196,813

[22] Filed: May 19, 1988

Related U.S. Application Data

[63] Continuation of Ser. No. 927,637, Nov. 6, 1986, abandoned.

[51] Int. Cl.⁴ ..................... G01N 25/22; G01N 27/50
[52] U.S. Cl. ................................ 436/116; 436/118; 436/152; 436/159; 436/160; 422/168; 422/177; 55/74; 55/387; 55/DIG. 30; 60/39.5; 60/276; 204/424; 204/429; 204/431; 204/432; 423/213.5; 423/239

[58] Field of Search ............... 436/116, 118, 152, 159, 436/160; 422/4, 168, 177; 55/74, 387, DIG. 30; 60/39.5, 276; 204/424, 429, 431, 432; 423/213.5, 239

[56] References Cited

U.S. PATENT DOCUMENTS 3,974,040  8/1976  Siebke et al. ................ 204/432 X
4,001,103  1/1977  Blurton et al. ............... 204/412 X
4,396,899  8/1983  Ohno ......................... 204/192.22 X Primary Examiner—Barry S. Richman
Assistant Examiner—Lynn M. Kummert
Attorney, Agent, or Firm—Peter Abolins; Clifford L. Sadler

[57] ABSTRACT

A structure and method for sensing oxides of nitrogen in a gas. The gas is first passed through an oxidation catalyst and any reducing species in the gas are oxidized. The output gas from the oxidation catalyst is received by a sensor which generates an output responsive to oxides of nitrogen because the sensor has been isolated from any reducing species in the gas.

8 Claims, 1 Drawing Sheet

OXIDES OF NITROGEN DETECTOR

This application is a continuation of application Ser. No. 927,637, filed 11/6/86 now abandoned.

BACKGROUND OF THE INVENTION

1. Field of the Invention

This invention relates to sensing oxides of nitrogen in an environment such as, for example, the exhaust flow from an internal combustion engine.

2. Prior Art

Various semiconductor gas sensors based on $SnO_2$ have been develoepd which exhibit sensitivity to oxides or nitrogen but, at the same time, also respond to a variety of other molecules such as carbon monoxide, hydrogen, hydrocarbons, etc. This lack of selectivity is particularly disadvantageous if such semiconductor gas sensor is used in connection with internal combustion engine control applications. That is, it is difficult to sense oxides of nitrogen in the exhaust from the engine because carbon monoxide, hydrogen, hydrocarbons and other reducing species are always present in the exhaust gas usually in greater concentrations than the oxides of nitrogen.

As a result, such known simple and inexpensive oxides of nitrogen sensors have limited use in control applications for internal combustion engines because of their inability to detect oxides of nitrogen in the presence of other gases. Such detection is desirable because the information can be used to provide information to aid and control the operation of the internal combustion engine. These are some of the problems this invention overcomes.

SUMMARY OF THE INVENTION

An apparatus for detecting oxides of nitrogen is a gas includes an oxidation catalyst and a sensor means. The oxidation catalyst means passes the gas an oxidizes any reducing species present in the gas. Thus, the sensor means is isolated from an reducing species in the gas and receives the gas passed by the oxidation catalyst means. The sensor means generates an output signal responsive to oxides of nitrogen in the gas.

An apparatus in accordance with an embodiment of this invention solves the problems of sensing oxides of nitrogen when mixed with other gases to which a semiconductor gas sensor may respond. The oxidation catalyst means oxidizes the reducing species. The $NO_2$ remains unaffected and the NO is oxidized to $NO_2$. Consequently, the gas in the catalyst contains only $NO_2$ which is then sensed by the sensor means. The result is an apparatus which detects oxides of nitrogen without being sensitive to reducing species such as carbon monoxide, hydrogen and hydrocarbons.

DETAILED DESCRIPTION OF THE INVENTION

Figure 1:
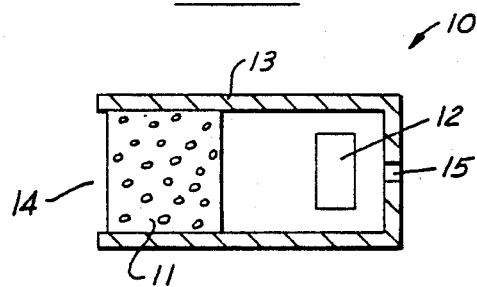
FIG. 1 is a schematic, generally cross section view of an apparatus in accordance with an embodiment of this invention.

Referring to FIG. 1, a detector 10 includes an oxidation catalyst 11 for passing a gas to a nonselective oxides of nitrogen sensor 12. Oxygen catalyst 11 and nonselective oxide sensor 12 are contained within a housing 13 having a frontal opening 14 for permitting a gas to enter detector 10, pass through oxidation catalyst 11 and then enter nonselective oxides of nitrogen sensor 12. Housing 13 has an optional rear opening 15 which permits the gas to pass through it. If housing 13 of detector 10 forms a section of the gas flow vessel so that all the gas flows through frontal opening 14, then the rear opening 15 is needed in order to allow the gas to pass. If detector 10 is simply immersed into the gas, then rear opening 15 is not always needed; if the sensor is heated and placed in a position so that the rear part of the sensor is higher than the front part, then gas is driven by convection through detector 10 from frontal opening 14 to rear opening 15 provided that a rear opening 15 exists. On the other hand, if gas is allowed to reach sensor 12 only by diffusion, then rear opening 15 is not needed.

Figure 2:
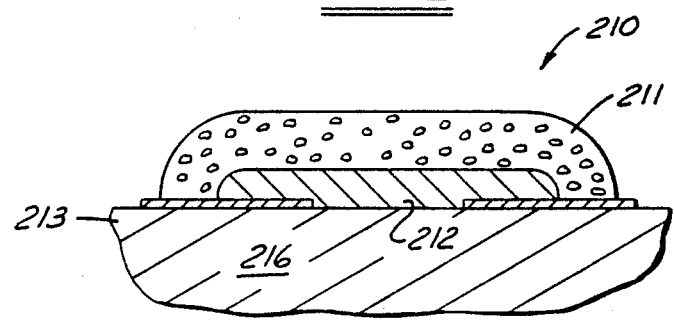
FIG. 2 is a cross section of an embodiment of this invention using an integrated structure.

Referring to FIG. 2, the structure of FIG. 1 has been made in an integrated structure so that a detector 210 includes an oxidation catalyst 211 which is formed over an oxide sensor 212. A substrate 216 acts as a support for detector 210 and is typically made of a material such as aluminum oxide. Two metal film electrodes 213 made, for example, from gold or platinum, are deposited on substrate 216 followed by the formation of metal oxide sensor 212 which is typically made of $SnO_2$ of ZnO. Advantageously, porous oxidation catalyst 2H is made of a material, such as alumina or spinel and is impregnated with an oxidation catalyst such as, for example, platinum or palladium. Porous oxidation catalyst 211 is deposited directly on metal oxide sensor 212.

In operation, gas coming inuto opening 14 of detector 10 of FIG. 1, contains oxides of nitrogen and reducing gases such as carbon monoxide, hydrogen, hydrocarbons, alcohols, etc. being carried in air or in an oxygen containing gas. This combined gas is first passed through porous oxidation catalyst 11. Oxidation catalyst 11 is heated to a temperature in excess of 200° C. such as, for example, in the range from about 300°–400° C. The reducing species are oxidized inside oxidation catalyst 11. However, the $NO_2$ remains unaffected and the NO is oxidized to $NO_2$. Consequently, the gas leaving oxidation catalyst 11 contains $NO_2$ which is then sensed by a nonselective oxides of nitrogen sensor 12. Operation of detector 210 of FIG. 2 is similar to the operation described above in connection with FIG. 1. The reducing species contained in the gas diffusing through porous catalyst 211 are removed by oxidation inside catalyst 211; the remaining $NO_2$ is then detected by sensor 212.

Proper operation of a device in accordance with an embodiment of this invention requires excess oxygen in the gas being sensed. That is, in an engine control application, the sensor can be used in connection with engine control strategies which provide for excess oxygen in the exhaust gas such as lean air fuel mixtures or the use of secondary air injected into the exhaust.

Various modifications and variations will no doubt occur to those skilled in the various arts to which this invention pertains. For example, the relative sizes of the substrate, the catalyst and the sensor may be varied from that disclosed herein. The resistive-type metal oxide sensor (e.g., $SnO_2$) shown in FIGS. 1 and 2 may be also replaced by another convenient (non-selective) $NO_x$ sensor such as a SAW (Surface-acoustic wave) sensor. These and all other variations which basically rely on the teachings through which this disclosure has advanced the art are properly considered within the scope of this invention.

We claim:

1. A method of sensing oxides of nitrogen in an ambient gas including other reducing gases including the steps of:

exposing an oxidation catalyst to ambient gas;

passing the ambient gas through the oxidation catalyst which oxidizes the reducing species without affecting any $NO_2$ present;

positioning the oxidation catalyst between the ambient gas and an oxides of nitrogen semiconductor sensor;

isolating the oxides of nitrogen semiconductor sensor from the ambient gas; and passing the gaseous output from the oxidation catalyst to the oxides of nitrogen semiconductor sensor to detect the amount of oxides of nitrogen by sensing the change in resistance of the oxides of nitrogen sensor.

2. A method as recited in claim 1 further comprising the step of heating the oxidation catalyst to a temperature in excess of about 200° C.

3. A method of sensing oxides of nitrogen as recited in claim 2 wherein the step of passing the gas through an oxidation catalyst includes applying the exhaust gas of an internal combustion engine to the oxidation catalyst.

4. An apparatus for detecting oxides of nitrogen in an ambient gas includes:

an oxidation catalyst means for passing ambient gas and oxidizing any reducing species present in the ambient gas and mounted so as to form an exterior surface of said apparatus exposed to the ambient gas, said oxidation catalyst means including a porous inert ceramic with metal oxidation catalyst particles deposited on walls of pores of said ceramics, said metal oxidation catalyst particles selected from the group consisting of Pd and Pt; and a sensor means mounted adjacent said oxidation catalyst means and shielded from said ambient gas so as to be exposed to an oxidized gas passing out of said oxidation catalyst means, and for receiving the oxidized gas passed by said oxidation catalyst means and generating an output responsive to oxides of nitrogen in the oxidized gas so that said sensor means is isolated from any reducing species in the ambient gas and said output is a function of oxides of nitrogen, said sensor means being fabricated of a semiconductor gas sensor selected from the group consisting of $SnO_2$ and ZnO.

5. An apparatus as recited in claim 1 wherein said oxidation catalyst means and said sensor means are formed as one integrated structure.

6. An apparatus as recited in claim 5 wherein said sensor means is a $SnO_2$ film and wherein said porous inert ceramic is deposited on the $SnO_2$ film.

7. An apparatus as recited in claim 6 wherein said ceramic is alumina.

8. An apparatus as recited in claim 6 wherein said ceramic is spinel.

* * * * *